(12) United States Patent
Klein et al.

(10) Patent No.: US 7,833,740 B2
(45) Date of Patent: Nov. 16, 2010

(54) TEST SYSTEM FOR DETECTING SALMONELLA

(75) Inventors: Harald Klein, Moerfelden (DE); Christoph von Eichel-Streiber, Schweppenhausen (DE)

(73) Assignee: TGC Biomics GmbH, Schweppenhausen (DE)

( * ) Notice: Subject to any disclaimer, the term of this patent is extended or adjusted under 35 U.S.C. 154(b) by 871 days.

(21) Appl. No.: 11/462,925

(22) Filed: Aug. 7, 2006

(65) Prior Publication Data

US 2007/0031906 A1   Feb. 8, 2007

Related U.S. Application Data

(60) Provisional application No. 60/707,551, filed on Aug. 12, 2005.

(30) Foreign Application Priority Data

Aug. 7, 2005   (DE) .................. 10 2005 037 796

(51) Int. Cl.
  *G01N 33/554* (2006.01)
  *G01N 33/569* (2006.01)
(52) U.S. Cl. ..................... 435/7.32; 435/7.35
(58) Field of Classification Search .................. None
  See application file for complete search history.

(56) References Cited

U.S. PATENT DOCUMENTS

2001/0009957 A1 * 7/2001 Oaks et al. .................. 530/395

FOREIGN PATENT DOCUMENTS

| WO | 97/18225 A | 5/1997 |
|---|---|---|
| WO | 00/23462 A | 4/2000 |
| WO | WO03/000935 A1 | 1/2003 |

OTHER PUBLICATIONS

Collazo et al. (Infection and Immunity, vol. 64, No. 9, pp. 3524-3531, Sep. 1996).*
Van Zijderveld et al. (Journal of Clinical Microbiology ,vol. 30, No. 10, pp. 2560-2566, Oct. 1992).*
Isogai et al. (Intern J Appl Res Vet Med, vol. 3, No. 4, 2005).*
Collazo et al. Molecular Microbiology, vol. 24,No. 4, pp. 747-756, 1997.*
Campell, Ailsa M.: "Monoclonal Antibodies" in Encyclopedia of Immunology, Academic Press, London, GB, vol. 3, 1992, pp. 1087-1091.
Musson Julie A. et al.: "Processing of viable *Salmonella typhimurium* for presentation of a CD4 T cell epitope from the Salmonella invasion protein C (SipC)" in European Journal of Immunology, vol. 32, No. 9, Sep. 2002, pp. 2664-2671.
Eichelberg Katrin et al.: "The flagellar sigma factor fliA (sigma 28) regulates the expression of Salmonella genes associated with the centisome 63 type III secretion system", in Infection and Immunity, vol. 68, No. 5, May 2000, pp. 2735-2743.
Komoriya, K. et al. : "Flagellar proteins and type III-exported virulence factors are the predominant proteins secreted into the culture media of *Salmonella typhimurium*" in Molecular Microbiology, Blackwell Science Ltd. , 34(4), 1999, pp. 767-779.
Watson, Patricia R. et al.: "Mutation of invH, but Not stn, Reduces Salmonella-Induced Enteritis in Cattle" in Infection and Immunity, American Society for Microbiology, Apr. 1998, pp. 1432-1438.
Collazo, Carmen M. et al.: "The invasion-associated type III System of *Salmonella typhimurium* directs the translocation of Sip proteins into the host cell" in Molecular Microbiology, Blackwell Science Ltd., 1997, 24(4), pp. 747-756.
Genebank: Accession No. U25631 of Sep. 5, 1995 (as of Mar. 3, 2006).
Komoriya et al., Flagellar proteins and type III-exported virulence factors are the predominant proteins secreted into the culture media of *Salmonella typhimurium*; Molecular Microbiology, vol. 34 p. 767, Nov. 1999.
Kaniga et al. Homologs of the Shigella IpaB and IpaC invasins are required for *Salmonella typhimurium* entry into cultured epithelial cells; J Bacteriol. Jul. 1995; 177(14): 3965-3971.
Weinrauch et al., Neutrophil elastase targets virulence factors of enterobacteria; Nature 417 (6884), 91-94 (May 2, 2002).
Hayward et al., Direct Nucleation and bundling of actin by the SipC protein of invasive Salmonella; EMBO J. Sep. 15, 1999; 18(18): 4926-4934.

* cited by examiner

*Primary Examiner*—Robert Mondesi
*Assistant Examiner*—Khatol Shahnan-Shah
(74) *Attorney, Agent, or Firm*—Joyce von Natzmer; Pequignot + Myers LLC

(57) ABSTRACT

Disclosed is a diagnostic test system for detecting *Salmonella* infections in a sample using monoclonal antibodies specific for SipC-protein.

8 Claims, 7 Drawing Sheets

M: molecular weight marker
1: rekombinant IpaC
2: rekombinant SipC

A: polyclonal SipC-Antiserum
B: monoclonal antibody I5B2
C: monoclonal antibody V1H7

M: molecular weight marker
1: recombinant SipC, C-terminal part, full extract
2: recombinant SipC, N-terminal part, full extract A: monoclonal antibody I5B2
B: monoclonal antibody V1H7

M: molecular weight marker
1: supernatant Salmonella brandenburg
2: supernatant S. typhi
3: supernatant S. typhimurium
4: supernatant S. enteritidis
5: supernatant S. infantis
6: supernatant S. bovismorbificans
7: supernatant S. paratyphi B
8: supernatant S. virchow
9: supernatant S. hadar
10: supernatant S. goldcoast

TEST SYSTEM FOR DETECTING SALMONELLA

CROSS REFERENCE TO RELATED APPLICATIONS

This application claims priority under 35 U.S.C. §119 to German patent application No. 10 2005 037 796.3, filed Aug. 7, 2005. This application also claims the benefit of U.S. provisional application No. 60/707,551, filed Aug. 12, 2005, which is incorporated herein by reference in its entirety.

Biological deposits under the Budapest Treaty were received at the Deutsche Sammlung von Mikroorganismen and Zellkulturen GmbH (DSMZ), Mascheroder Weg 1b, D-38124 Braunschweig, Germany on Jun. 1, 2006. The deposits were identified as V1H7 and I5B2, respectively and given accession numbers DSM ACC2789 (V1H7) and DSM ACC2790 (I5B2), respectively.

FIELD OF THE INVENTION

The invention relates to a diagnostic test system for detecting *Salmonella* infections in a sample.

BACKGROUND

*Salmonella* are mobile, gram-negative, rod-shaped bacteria. The taxonomic classification of *Salmonella* is based on their somatic (O) antigens and flagellar (H) antigens according to the Kaufmann-White system (a diagnostic antigen table) and results in a classification system in which *Salmonella* are declared as serovars and are characterized and classified on the basis of a sero formula. Of the more than 2400 *Salmonella* serovars known, only twenty to thirty are so far of importance in practice as pathogens in epidemiological diseases. These include the pathogens causing typhoid (*S. typhi*) and paratyphoid (*S. paratyphi* A, *S. paratyphi* B, *S. paratyphi* C) and a large number of enteritis pathogens, the so-called "enteritis *Salmonella*." Whereas the typhoid and paratyphoid *Salmonella* cause serious generalized systematic infections, i.e., infections involving the entire body, an infection with enteritis *Salmonella* is usually limited locally to the intestines.

Salmonellosis in humans is usually a food-borne disease. The infection generally occurs due to consumption of infected or contaminated foods, whereas transmission to humans through direct contact with animals shedding *Salmonella* is rare. Direct or indirect human-to-human transfer may take place as a nosocomial infection in predisposed patients or under unfavorable hygiene conditions.

Primary sources of infection include in particular foods originating from poultry, cattle and swine, the animals themselves being sick only in extremely rare cases. Consequently, detection of the pathogens and/or antibodies plays a crucial role not only in human medicine but also in food operations and in veterinary medicine. The infectious dose for an adult human is $10^4$ to $10^6$ microorganisms. The incubation time is 5-72 hours and depends on the size of the infectious dose.

In a case of an enteritis *Salmonella* infection, a so-called enteritis salmonellosis, the infection usually manifests itself with diarrhea, nausea or vomiting and moderate fever. The symptoms usually last only a few hours or days. In weakened patients, however, this disease may also be fatal.

Shedding of enteritis *Salmonella* usually lasts an average of three to six weeks but in infants it may continue for several months.

In patients with a pre-existing congenital burden, *Salmonella* may trigger a reactive arthritis as a secondary illness 2-6 weeks after the enteritis infection; in rare cases, this arthritis may assume a chronic manifestation. At this point in time, no pathogens are usually detectable and/or culturable, so serological methods (Widal agglutination, see below) play a major role in detecting a past *Salmonella* infection (i.e., with manifestations in the past).

Under the German Infection Prevention Act, a tentative diagnosis or manifestation of acute infectious gastroenteritis must be reported under certain circumstances; ditto for detection of *Salmonella*. Furthermore, there are various legal requirements in Germany and other EU countries concerning required measures for combating *Salmonella* (e.g., Bovine *Salmonella* Regulations, Poultry *Salmonella* Regulations, various regulations of the feed and food law). In addition, various *Salmonella* monitoring programs have been established as part of self-monitoring in production.

The main point of emphasis in clinical laboratory diagnostic methods for salmonelloses is in culturing pathogens from fecal stool specimens and classifying them as suspected cases of *Salmonella* with the help of omnivalent and/or polyvalent *Salmonella* infectious sera. As a rule, such a tentative diagnosis can only be made approximately one to two days after receiving the sample in the diagnostic laboratory. In most cases another 2-3 days are needed for a confirmed diagnosis of *Salmonella* infection. In this period of time, suspected individual clones are characterized biochemically (colored series) and serologically. For serological differentiation, O and H antigens are analyzed in the form of microscope slide agglutination (Kaufmann-White system). This is done by first using polyvalent *Salmonella* test sera to determine the precise antigen formula with monovalent O and H antisera. As a rule, a total of 3-5 days are therefore needed for definitive detection of a *Salmonella* infection. In a case of salmonellosis caused by contaminated food in particular, the long amount of time required to obtain a diagnosis is a major problem because other people may become infected in the meantime. Therefore, in a suspected case of *Salmonella* infection, the source of infection must be localized and further dissemination prevented. In addition, patients are also isolated to prevent transmission of the infection. Early diagnosis is of great importance for the success of this measure.

Serological detection of *Salmonella* antibodies plays a major role in veterinary medicine and in the food industry, especially in the form of ELISA systems. For example, in Germany as well as in neighboring countries, the *Salmonella* antibody status (mainly anti-LPS immunoglobulin) of animal populations is currently being monitored in particular. Detection is performed on blood or meat juices. However, this method has limitations because it cannot reliably detect all pathogenic *Salmonella* serovars.

In human medicine however, especially in typhoid *Salmonella* infections, the so-called Widal agglutination test in particular is used to supplement bacteriological detection of the pathogen. In this test, patient serum is combined with boiled (O-antigen agglutination) or formalinized (H-antigen agglutination) *Salmonella* suspensions and tested for agglutination of the bacteria. One disadvantage of this is that not all infections are associated with the development of an Anti-O-Antigene titer; secondly, antibodies to H antigens may persist for many years after an infection. However, titer against O antigenes usually drop off again after a few weeks. It is thus impossible to reliably differentiate between an acute infection and an infection that has already been overcome.

Under in vitro culture conditions, *Salmonella* secretes a panel of proteins into the ambient medium. One of these proteins is the SipC protein.

The publications and other materials, including patents, used herein to illustrate the invention and, in particular, to provide additional details respecting the practice are incorporated herein by reference in their entirety.

The nucleotide sequence of the SipC gene is known and is available to those skilled in the art via gene databanks (e.g., accession no.: U25631 or X82670). WO 03/000935 (see also U.S. Patent Publication 20030022214) discloses the use of PCR primers and FRET hybridization probes against the SipC gene for detection of *Salmonella*. However, this publication does not mention the use of SipC protein for the same purpose, in particular the use of antibodies to SipC protein.

In Weinrauch et al. "Neutrophil Elastase Targets Virulence Factors of Enterobacteria" (*Nature* 2002, 417, 6884, 91-4) and Hayward et al. "Direct nucleation and bundling of actin by the SipC protein of invasive *Salmonella*" (*EMBO J.* 1999, 18, 18, 4926-34) the use of a polyclonal antibody to SipC protein for detection thereof in Immunoblot is described.

However, the polyclonal antibodies described there are not monospecific for *Salmonella* and therefore are not suitable for specific detection of *Salmonella*—as required especially in human diagnostics and in food testing.

In the context of the present invention, it has surprisingly been found (1.) that the SipC protein is a highly preserved molecule, i.e., there are only minor differences among the amino acid sequences of various *Salmonella* serovars, and (2.) that *Salmonella* already at a very early point in time produce the proteins of the typ-III-secretion system.

There is a need in the art for a *Salmonella* detection system that is capable of providing a rapid and reliable yes or no answer to the question of whether a certain sample is currently infected with *Salmonella* or whether there has been an infection in the past.

BRIEF SUMMARY OF THE INVENTION

One method of meeting this need comprises providing a diagnostic test system for detecting *Salmonella* in a sample containing at least one monoclonal antibody that reacts specifically with the *Salmonella* SipC protein.

In one embodiment the present invention provides a test system for detection in a sample of a current and/or past *Salmonella* infection which comprises (a) providing at least one monoclonal antibody specific for SipC-protein of *Salmonella* spp., (b) contacting said sample with said at least one monoclonal antibody, (c) assessing binding of said at least one monoclonal antibody to any SipC-protein of *Salmonella* spp. in said sample to detect said current and/or past *Salmonella* infection.

This monoclonal antibody is preferably the monoclonal antibody produced by the hybridoma cell line with lab code I5B2 deposited on Jun. 1, 2006 under the number DSM ACC2790 with the DSMZ (German Collection of Microorganisms and Cell Cultures GmbH, Germany), or the monoclonal antibody produced by the hybridoma cell line with lab code V1H7 deposited on Jun. 1, 2006 under the number DSM ACC2789 with the DSMZ (German Collection of Microorganisms and Cell Cultures GmbH, Germany).

In diagnostic use, this test system advantageously recognizes in one embodiment a wide variety of *Salmonella*, regardless of the specific serovar type, owing to the specific monoclonal antibody/antibodies and consequently permits a detection of *Salmonella* that goes beyond the serovar.

This is not possible with methods now commonly used as these methods are generally based on detection of O and H antigens which may occur in high variability and a wide variety of combinations in the individual *Salmonella* serovars.

In certain embodiments, the inventive test system allows *Salmonella* to be detected just a few hours after the *Salmonella* infection and/or after occurrence of the first symptoms, and can do so with a reliable result, so that measures to combat *Salmonella* can be taken at a very early point in time.

The proposed test system is preferably an ELISA (enzyme-linked immunosorbent assay). In particular, with the monoclonal antibodies produced by hybridoma cell lines I5B2 (DSM ACC2790) and V1H7 (DSM ACC2789) described herein for the first time, it was possible for the first time to establish an ELISA test that reacts specifically with *Salmonella* and does not cross-react with *Salmonella*-related bacteria, in particular not with *Shigella* or enteropathogenic *E. coli*.

In one preferred embodiment of the present invention, a test system for detecting antibodies to *Salmonella* in a sample is provided that comprises as the reagent recombinantly produced SipC protein or native SipC protein isolated from *Salmonella*.

Compared with the detection of antibodies in human medicine by means of Widal agglutination, the test system of the present invention advantageously provides in certain embodiments that immunoglobulins to a preserved *Salmonella* antigen, namely the SipC protein, are detected in a manner that goes beyond the serovar, thus achieving increased sensitivity of the test. In addition, the inventive test system, in particular in the embodiment as an ELISA test, supplies objective measurement results. In particular, the results no longer depend on the subjective eye of the observer, as it is the case when an agglutination reaction is read. In contrast with the Widal reaction, which can take up to 18 hours to perform, ELISA yields test results after only a few hours. In preferred embodiments, the present invention provides results within less than about 8 hours, less than about 7 hours, less than about 6 hours and less than about and/or about 5 hours.

In addition, the test system may be used for detecting an anti-SipC titer in meat, serum or other body fluids of commercial animals as well as in eggs. Meat juice(s) from commercial animals as a sample may serve here as an example. The meat juice is obtained by methods with which those skilled in the art are familiar and then is tested for anti-SipC antibodies, e.g., in the ELISA test with added SipC protein as a scavenger molecule.

Suitable test systems in the sense of the present invention include in particular ELISA, sandwich ELISA, Western Blot, latex agglutination, line blot and other methods familiar to the skilled artisan.

This invention is explained in greater detail below on the basis of exemplary embodiments and figures.

BRIEF DESCRIPTION OF THE DRAWINGS

The figures show:

FIG. 1A: Lane 1=*Salmonella hadar*, Lane 2=*S. brandenburg*, Lane 3=*S. goldcoast*, Lane 4=*S. senftenberg*, Lane 5=*S. virchow*.

FIG. 1B: Lane 1=*S. typhimurium*, Lane 2=*S. enteritidis*, Lane 3=*S. infantis*, Lane 4=*S. bovis morbificans*

Negative control=culture medium;

Positive control=50 ng and 5 ng abs. recombinant SipC.

Figure 7:
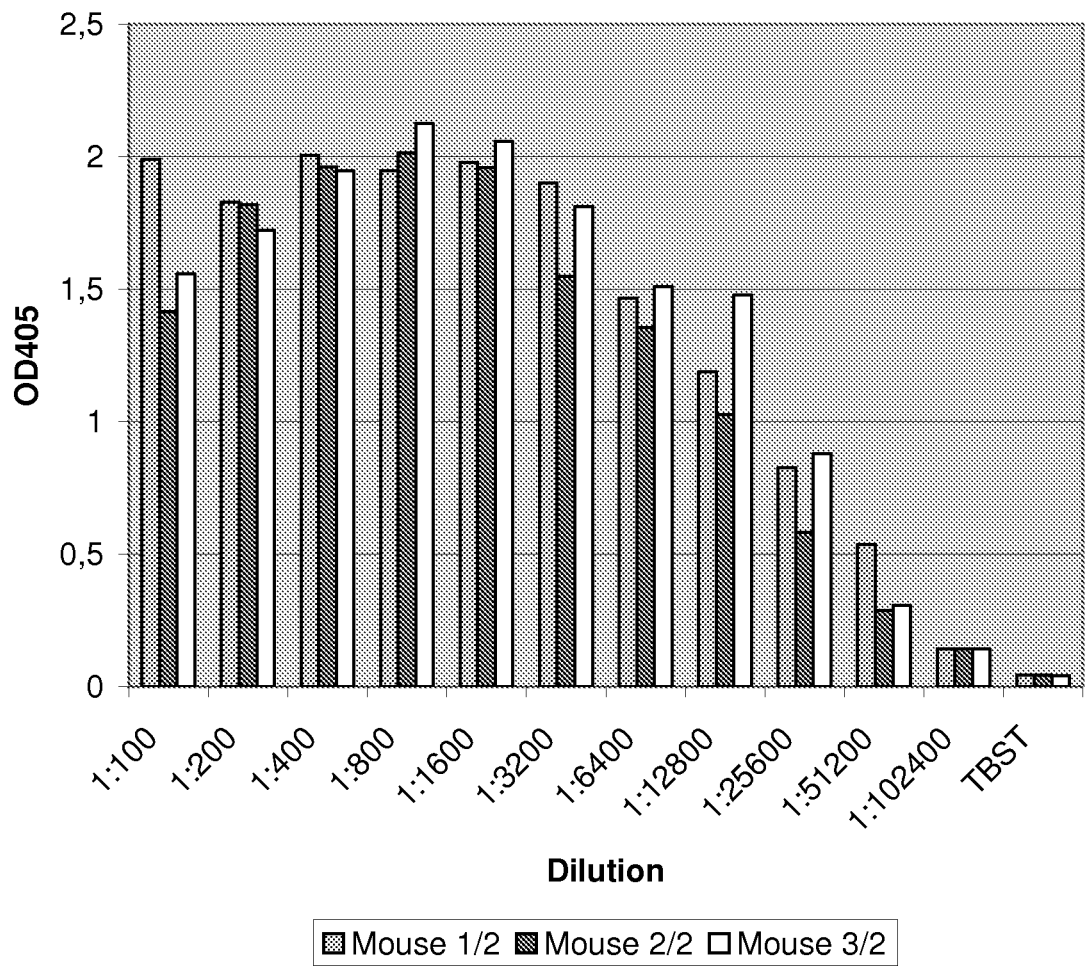

FIG. 7: Titration of sera (after the first booster vaccination) of mice vaccinated with recombinant SipC protein negative control;

Negative control=pooled pre-immune serum.

DETAILED DESCRIPTION OF VARIOUS AND PREFERRED EMBODIMENTS OF THE INVENTION

Those skilled in the art will be familiar with all the methods mentioned in the examples, which are described in Ausubel et al. (2003), for example. As those skilled in the art will understand, the scope of the present invention extends beyond the specific antibodies described herein. Non-limiting examples are antibody fragments such as single-chain antibodies (see, for example, U.S. Pat. Nos. 7,084,258 and 7,081,520) which are directed at SipC.

Example 1

Preparing Monoclonal Antibodies Which React Specifically With the SipC Protein of *Salmonella* (*Salmonella* SipC Protein)

Genomic bacterial DNA was isolated from the *Salmonella* strain *Salmonella enterica* serovar enteritidis and the SipC gene was amplified and cloned with the help of SipC-specific primers.

On the basis of a subsequent sequence analysis and database comparison, confirmation that the cloned DNA fragment is the reading frame that codes for SipC was obtained. The calculated molecular weight of the derived SipC protein is approximately 42 kDa.

After subcloning in pET30a expression vector (NOVAGEN)—or some other suitable expression vector—the antigen was produced recombinantly in *E. coli* in fusion with histidine tag and then purified by affinity chromatography.

The purity of the antigen obtained in this was sufficient for use in immunization of rabbits and mice.

Several mice received basic vaccinations with the recombinant *Salmonella* antigen SipC described above and then received two booster vaccinations. The spleen cells (antibody-producing B-lymphocytes) of these animals that were isolated were then fused with myeloma cells (from a tumor cell line that is capable of unlimited growth but no longer produces antibodies) and the resulting hybridomas were selected and cloned. Individual clones were then screened immunologically for production of specific monoclonal antibodies to the recombinant SipC antigen used for vaccination. In this screening, two monoclonal antibodies produced by the hybridoma cell lines I5B2 and V1H7 were obtained. On Jun. 1, 2006, these hybridoma cell lines were deposited under the numbers DSM ACC2790 (I5B2) and DSM ACC2789 (V1H7) with the DSMZ (German Collection of Microorganisms and Cell Cultures, Germany). The respective monoclonal antibodies are referred to herein as monoclonal antibodies I5B2 and V1H7.

For comparative experiments, a polyclonal antibody was produced with the same recombinant *Salmonella* antigen SipC as that described above. To do so, rabbits first received basic vaccinations and then several booster vaccinations. Finally, a polyclonal antiserum was obtained from the blood of the rabbits.

Figure 2:
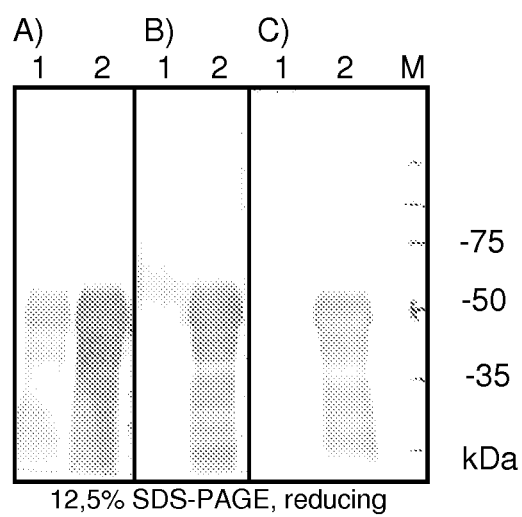
FIG. 2: Western Blot strips after reaction of polyclonal SipC antiserum (A), monoclonal antibody I5B2 (B) and monoclonal antibody V1H7 (C) with recombinant *Salmonella* SipC protein (lane 2) and recombinant *Shigella* IpaC protein (lane 1).

The specificity of the monoclonal and polyclonal antibodies thus obtained was tested in Western Blot. FIG. 2 shows Western Blot strips developed with the polyclonal SipC antiserum (A) described above, monoclonal antibody I5B2 (B) and monoclonal antibody V1H7 (C) described above. Recombinant IpaC (lane 1) and recombinant SipC (lane 2) were used as probes. IpaC antigen is a protein having a homologous sequence from *Shigella flexneri* bacterium. In contrast with the polyclonal antiserum, which also cross-reacts with the homologous IpaC protein from *Shigella* (FIG. 2A), the monoclonal antibodies I5B2 and V1H7 are specific for the *Salmonella* antigen SipC (FIGS. 2B and C).

Figure 3:
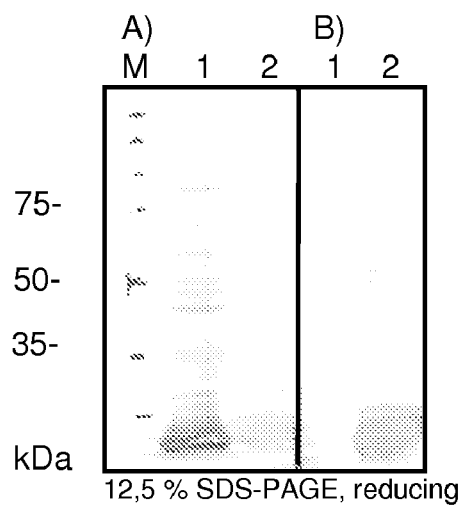
FIG. 3: Western Blot strips after reaction of partial fragments of *Salmonella* SipC antigen with monoclonal antibodies I5B2 (A) and V1H7 (B). The C-terminal region of SipC (amino acids 252-410) is applied to lane 1 and the N-terminal region of SipC (amino acids 1-200) is applied to lane 2.

To investigate whether monoclonal antibodies I5B2 and V1H7 are directed against different epitopes of the SipC gene, subfragments of the *Salmonella* antigen were produced recombinantly and were detected by Western Blot using the monoclonal antibodies. FIG. 3 shows suitably developed Western Blot strips, whereby a whole bacterial extract containing the C-terminal half of SipC (amino acids 252-410) was applied to lane 1 and whole bacterial extract containing the N-terminal region of SipC (amino acids 1-200) was applied to lane 2. It is found that the two monoclonal antibodies are definitely directed against different SipC epitopes because monoclonal antibody I5B2 (FIG. 3A) reacts with the C-terminal SipC fragment, whereas monoclonal antibody V1H7 (FIG. 3B) reacts with the N-terminal half of SipC.

Example 2

Detection of Various *Salmonella* Serovars Using Polyclonal Antiserum Against Recombinantly Produced *Salmonella* SipC Protein LB medium (LB=Luria broth) in 3 mL portions was inoculated with a single bacterial colony of the *Salmonella* strains listed in column 1, Table 1 and incubated for 16 hours at 37° C. while agitating lightly.

Then the bacteria were separated by centrifugation and the resulting supernatant was precipitated with a final concentration of 10% TCA on ice.

After a washing step with ice-cold acetone (−20° C.), the protein pellet was dried, re-suspended in SDS gel-sample buffer, boiled and separated by gel electrophoresis on a 12.5% SDS gel.

The proteins were transferred to a PVDF membrane by semi-dry blotting. The membrane was developed after saturation of all nonspecific binding sites first with polyclonal SipC antiserum (dilution 1:10,000) prepared according to example 1 and then with a secondary antibody directed against rabbit immunoglobulin and labeled with alkaline phosphatase.

Figure 1:
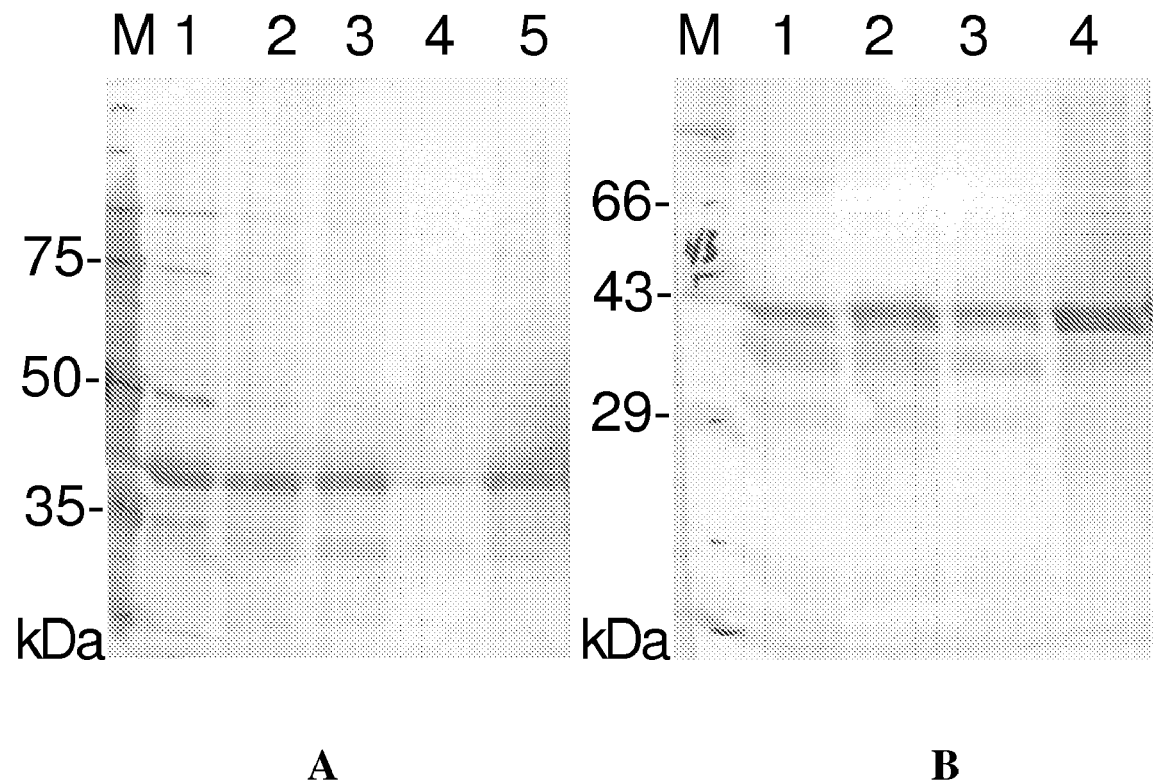
FIG. 1: Western Blot analysis of culture supernatants of various *Salmonella* serovars with polyclonal antiserum to SipC. The proteins secreted by the bacteria in the culture supernatant were separated after TCA precipitation on a 10% SDS gel (FIG. 1A) or a 12.5% SDS gel (FIG. 1B) and were then transferred to PVDF membranes. Immunological detection was performed using polyclonal SipC antiserum (1:10,000) and alkaline-phosphatase-labeled anti-rabbit antibody (Dianova 1:30,000). Molecular weight standards are shown on the left side of the figure.

The result of this Western Blot is shown in FIG. 1: With all the *Salmonella* strains tested a definite main band is detectable in the molecular weight range of 42 kDa, i.e., in the calculated molecular weight range of the SipC protein.

This means that SipC protein is produced by all the *Salmonella* strains mentioned in Table 1 and is secreted in the supernatant. In addition, this experiment shows that SipC protein/gene is highly preserved in a manner that goes beyond the specific serovar.

This surprising finding shows that SipC protein is especially suitable for an immunological method of detecting *Salmonella* that goes beyond the specific serovar.

Example 3

Immunological Detection of the SipC Antigen In Supernatants of Various Clinical *Salmonella* Isolates Using ELISA And Western Blot For immunological detection of SipC antigen from culture supernatants of clinical *Salmonella* isolates, 5 mL portions of LB medium were inoculated with a bacterial colony and incubated overnight at 37° C. while agitating gently. Table 2 lists the *Salmonella* strains used in this process, each characterized according to the Kaufmann-White system.

The bacterial cultures were centrifuged the next morning at 4000×g (15 min, 4° C.); the supernatants thus obtained were sterile-filtered through a 0.22 µm membrane and then used in the diagnostic assays (ELISA, Western Blot).

A) ELISA Method of SipC Detection From Bacterial Culture Supernatants:

ELISA plates were coated with monoclonal antibody I5B2 described in Example 1 (1 µg/well). After blocking non-specific binding sites with 20% gelatin solution, 150 µL of bacterial cell culture supernatant was pipetted into each well. A defined amount of recombinant SipC protein (5 ng/well) was used as the positive control; sterile culture medium plus culture supernatant of other enteropathogenic bacterial species (*Escherichia coli, Yersinia enterocolitica*) treated in the same way was used as the negative controls. The plates were incubated for one hour at 37° C. and then washed with TBST (Tris-buffered saline Tween 20). For detection of the bound antigen, the polyclonal SipC antiserum described in Example 1 was used in a dilution of 1:50,000 after protein G purification (concentration 4 mg/mL). After a renewed washing step with TBST, there followed a one-hour incubation with an alkaline phosphatase-labeled conjugate, which was then removed by washing again with TBST. By adding the 4-nitrophenyl phosphate substrate (dissolved in alkaline phosphatase buffer, 1 mg/mL) and subsequently reacting it in a reaction catalyzed by antibody-coupled alkaline phosphatase, specifically bound antibody conjugate was visualized colorimetrically and the optical density was determined at 405 nm after a reaction time of 30 minutes.

Figure 4:
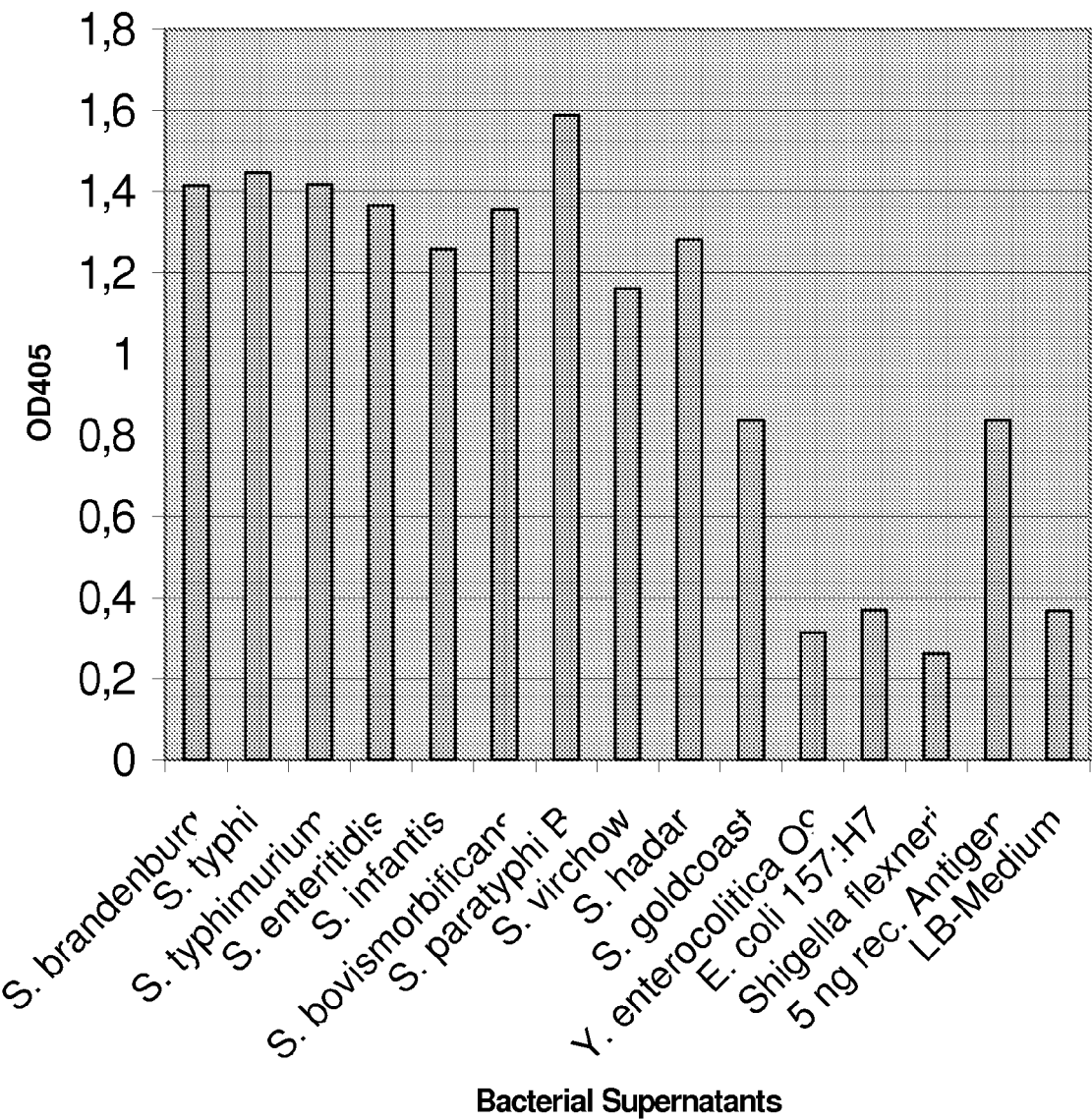
FIG. 4: Detection of SipC protein in various *Salmonella* culture supernatants by ELISA: *Salmonella brandenburg, S. typhi, S. typhimurium, S. enteritidis, S. infantis, S. bovismorbificans, S. paratyphi* B, *S. virchow, S. hadar, S. goldcoast, Y. enterocolitica* 09, *E. coli* 157:H7, *Shigella flexneri;* 5ng rec. antigen; LB-medium.

As FIG. 4 shows, all the *Salmonella* culture supernatants tested give a positive reaction in the ELISA test, whereas the extinction of identically treated supernatants of other bacterial enteropathogens (*E. coli, Yersinia enterocolitica, Shigella flexneri*) corresponds to the extinction of sterile culture medium.

B) Western Blot Nethod of SipC Detection In Bacterial Culture Supernatants:

15 µL of the bacterial cell supernatants obtained was separated on 10% SDS-polyacrylamide gel and then transferred by the semi-dry blotting method to a PVDF membrane. Non-specific binding sites were blocked with 3% BSA (bovine serum albumin) in TBST. Then the batch was incubated with SipC-specific monoclonal antibody I5B2 (350 µg/mL after protein-G purification, 1:100 diluted in TBST). After three washing steps with TBST, the membrane was incubated with an alkaline phosphatase anti-mouse conjugate for one more hour and then washed repeatedly with TBST. It was developed by adding substrate in the form of BCIP (5-bromo-4-chloro-3-indolyl phosphate p-toluidinium salt, 50 mg/mL in 100% dimethyl formamide, 1:300 in alkaline phosphatase buffer) and in NBT (50 mg/mL nitroblue tetrazolium in 70% dimethyl formamide, 1:150 in alkaline phosphatase buffer) for five minutes at room temperature.

Figure 5:
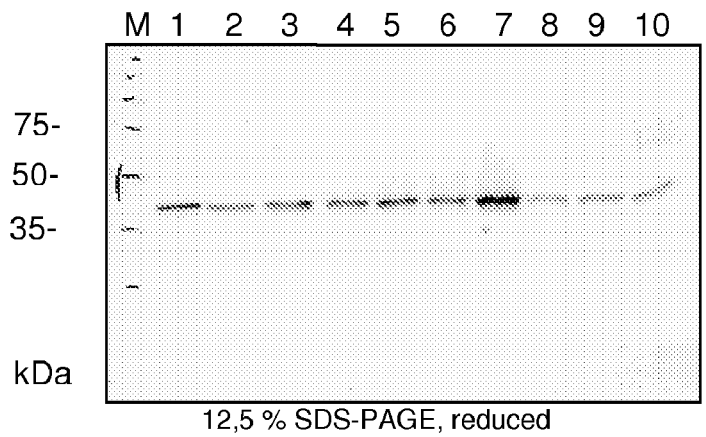
FIG. 5: Detection of SipC protein in various *Salmonella* culture supernatants by Western Blot. M=molecular weight marker, 1=supernatant of a culture of *Salmonella brandenburg,* 2=supernatant of a culture of *S. typhi,* 3=supernatant of a culture of *S. typhimurium,* 4=supernatant of a culture of *S. enteritidis,* 5=supernatant of a culture of *S. infantis,* 6=supernatant of a culture of *S. bovismorbificans,* 7=supernatant of a culture of *S. paratyphi* B, 8=supernatant of a culture of *S. virchow,* 9=supernatant of a culture of *S. hadar,* 10=supernatant of a culture of *S. goldcoast.*

The signals of the Western Blot illustrated in FIG. 5 correlate very well with the ELISA data described previously. Here again, all the tested *Salmonella* culture supernatants have a positive reaction with the monoclonal antibody I5B2 in the expected size range of 42 kDa. Furthermore, there is a good correlation between the intensity of the Western Blot signals and the measured extinctions in ELISA. Thus, for example, the supernatant of *S. paratyphi* B has the highest reactivity in both cases.

Example 4

Time-Dependent Immunological Detection of SipC Antigen In Culture Supernatants of *Salmonella Enteritidis* And *S. Typhimurium*

As shown in Example 3, SipC ELISA is a highly specific and sensitive test method for detecting different strains of *Salmonella*. With the present Example 4, it is examplatory shown that this SipC ELISA also has the advantageous property that it can be performed (used) at a very early point in time in a presumed *Salmonella* infection as SipC protein is formed and is efficiently detectable at a very early point in time.

The following procedure was used to demonstrate SipC expression over time:

20 mL LB medium was inoculated with a bacterial colony and incubated at 37° C. while agitating. A sample was taken once an hour for nine hours and then centrifuged; the sterile-filtered supernatant was tested for the presence of SipC protein using the ELISA method described in Example 3(A).

Figure 6:
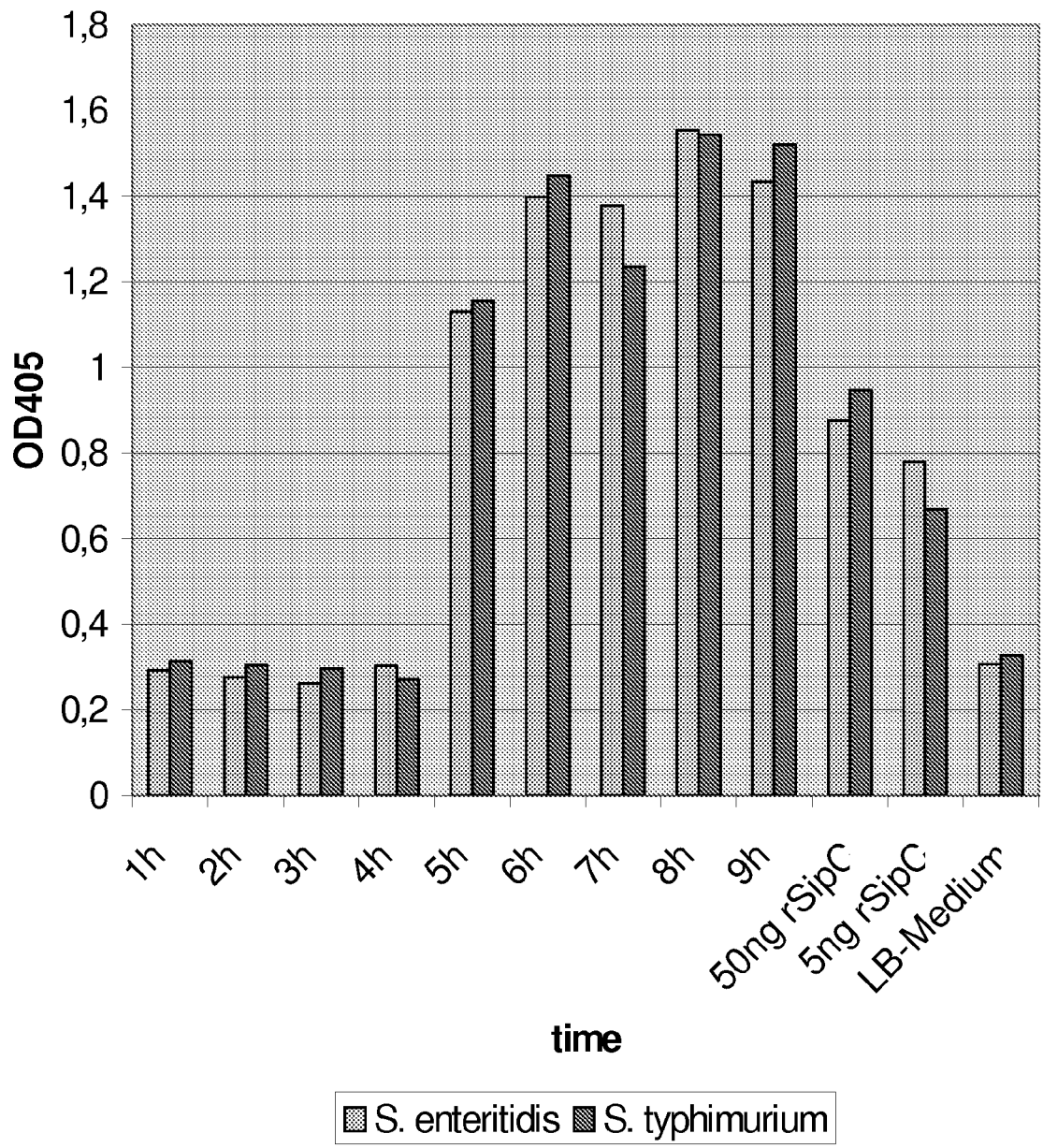
FIG. 6: Time-dependent immunological detection (ELISA) of SipC antigen in culture supernatants of *Salmonella enteritidis* and *S. typhimurium*.

The results of this experiment are depicted in FIG. 6. It can be seen from FIG. 6 that SipC protein can be detected in the supernatant for the first time specifically five hours after the start of the culture. During the next four hours, there was no further measurable in- or decrease in the amount of SipC protein.

Surprisingly, the proteins of the type III secretion system are already formed at a very early point in time.

On the basis of all this, SipC ELISA is excellently suited for rapid detection of *Salmonella*.

Example 5

Immunological Detection of SipC Antibodies In ELISA

To test on whether SipC antibodies can be detected in the blood of infected animals, an experiment was conducted to determine how efficiently SipC induces the formation of antibodies.

To do so, recombinant SipC protein was administered to three mice. Then a small amount of blood was taken and titrated out in a specific ELISA directed against SipC antibodies (see FIG. 7). To do so, 1 μg recombinant SipC protein per well was applied to an ELISA plate and then nonspecific binding sites were blocked with a 20% gelatin solution and finally incubated with the dilution steps of the sera shown in FIG. 7. Detection of specifically bound antibodies was performed with the help of an alkaline phosphatase-labeled anti-mouse conjugate using methods with which those skilled in the art are familiar. After adding 4-nitrophenyl phosphate as a substrate for the antibody-linked alkaline phosphatase, the specifically bound antibody conjugate was visualized calorimetrically on the basis of the substrate reaction, and after a reaction time of 30 minutes, the optical density was determined at 405 nm (as a measure of the amount of substrate reacted and/or bound antibody conjugate).

FIG. 7 shows that the serum of all three mice could be diluted to a great extent (up to approx. 1:50,000). The strength of the immune response to the protein was almost identical in all three mice.

These results show that SipC is a highly immunogenic protein (=protein with a high antigenicity), which triggers a definite immune response in all infected animals, namely an efficient and specific antibody response to SipC protein.

With the help of ELISA for detection of specific SipC antibodies, this makes possible for the first time a determination of the anti-SipC titer in the serum of infected humans or animals. Similarly, anti-SipC antibodies in meat juices from commercial animals can be detected. ELISA for detection of SipC antibodies is thus a specific and efficient test method for identification of current or previous *Salmonella* infections.

While the invention has been described in the form of specific embodiments, it will be understood that it is capable of further modifications and this application is intended to cover any variations or adaptations within the skill of the person skilled in the art.

TABLE 1

Listing of *Salmonella* Serovare and their Antigene formula (Kauffmann-White-Schema) used in Example 2

| | | Flagellar-Antigene H | |
|---|---|---|---|
| *Salmonella*-Strain | O-Antigene | Phase 1 | Phase 2 |
| S. hadar | 6, 8 | $z_{10}$ | e, n, x |
| S. brandenburg | 1, 4, 12, 27 | l, v | e, n, $z_{15}$ |
| S. goldcoast | 6, 8 | r | l, w |
| S. senftenberg | 1, 3, 19 | g, [s], t | — |

TABLE 1-continued

Listing of *Salmonella* Serovare and their Antigene formula (Kauffmann-White-Schema) used in Example 2

| | | Flagellar-Antigene H | |
|---|---|---|---|
| *Salmonella*-Strain | O-Antigene | Phase 1 | Phase 2 |
| S. virchow | 6, 7 | r | 1, 2 |
| S. typhimurium | 1, 4, [5], 12 | i | 1, 2 |
| S. enteritidis | 1, 9, 12 | [f], g, m, [p] | [1, 7] |
| S. infantis | 6, 7, 14 | r | 1, 5 |
| S. bovis morbificans | 6, 8 | r, [i] | 1, 5 |

TABLE 2

Listing of *Salmonella* Serovare and their Antigene formula (Kauffmann-White-Schema) used in Example 4

| | | Flagellar-Antigene H | |
|---|---|---|---|
| *Salmonella*-Strain | O-Antigene | Phase 1 | Phase 2 |
| S. hadar | 6, 8 | $z_{10}$ | e, n, x |
| S. brandenburg | 1, 4, 12, 27 | l, v | e, n, $z_{15}$ |
| S. goldcoast | 6, 8 | r | l, w |
| S. virchow | 6, 7 | r | 1, 2 |
| S. typhimurium | 1, 4, [5], 12 | i | 1, 2 |
| S. enteritidis | 1, 9, 12 | [f], g, m, [p] | [1, 7] |
| S. infantis | 6, 7, 14 | r | 1, 5 |
| S. bovis morbificans | 6, 8 | r, [i] | 1, 5 |
| S. typhi | 9, 12, [vi] | d | — |
| S. pararyphi B | 1, 4, [5], 12 | [b] | [1, 2] |

REFERENCES

Komoriya K. et al.: Flagellar proteins and type III-exported virulence factors are the predominant proteins secreted onto the culture media of *Salmonella typhimurium*. Mol. Microbiol. (1999), 34 (4), 767-779

Hueck C. J. et al.: *Salmonella typhimurium* secreted invasion determinants are homologous to *Shigella* Ipa proteins. Mol. Microbiol. (1995), 18 (3), 479-490

Hueck C. J.: Type III protein secretion systems in bacterial pathogens of animals and plants. Microbiol. Mol. Biol. Rev. (1998), 379-433

Daefler, S.: Type III secretion by *Salmonella typhimurium* does not require contact with a eukaryotic host. Mol. Microbiol. (1999), 31 (1), 45-51

Medical Microbiology and Infectiology. H. Hahn, D. Falke, S. H. E. Kaufmann, U. Ullmann (eds.), Springer Verlag Berlin Heidelberg New York, Third Edition 1999.

Kaniga K. et al.: Homologs of the *Shigella* IpaB and IpaC invasins are required for *Salmonella typhimurium* entry into cultured epithelial cells. J. Bacteriol. (1995), 177 (14), 3965-3971.

Thomson, G. T. et al.: Serological testing for reactive arthritis. Clin. Invest. Med. (1994), 17 (3), 212-217.

Van der Heijden, H. M.: First international ring trial of ELISAs for *Salmonella* antibody detection in swine. Berl. Munch. Tierärztl. Wochenschr. (2001), 114 (9-10), 389-392.

Ausubel, F. M. et al.: Current Protocols in Molecular Biology (2003), John Wiley and Sons. Inc.

We claim:

1. Process for detecting a current and/or past *Salmonella* infection in a sample comprising
    (a) providing at least one monoclonal antibody specific for SipC-protein of *Salmonella* spp., (b) contacting said sample with said at least one monoclonal antibody, (c) assessing binding of said at least one monoclonal antibody to any SipC-protein of *Salmonella* spp. in said sample to detect said current and/or past *Salmonella* infection, wherein said at least one monoclonal antibody is produced by hybridoma cell line V1H7, Accession No. DSM ACC2789, deposited with DSMZ on Jun. 1, 2006 or by hybridoma cell line I5B2, Accession No. DSM ACC2790, deposited with DSMZ on Jun. 1, 2006.

2. The process of claim 1, wherein said infection is a past infection.

3. The process of claim 1, wherein said at least one monoclonal antibody is produced by hybridoma cell line V1H7, Accession No. DSM ACC2789, deposited with DSMZ on Jun. 1, 2006.

4. The process of claim 3, wherein the system is an ELISA.

5. The process of claim 1 wherein said at least one monoclonal antibody is produced by hybridoma cell line I5B2, Accession No. DSM ACC2790, deposited with DSMZ on Jun. 1, 2006.

6. The process of claim 5, wherein the system is an ELISA.

7. The systcm process of claim 1, wherein said current and/or past *Salmonella* infection is detected after less than about 8 hours of contacting in (b).

8. The systcm process of claim 7, wherein said current and/or past *Salmonella* infection is detected after less than about 6 hours of contacting in (b).

* * * * *